United States Patent
Hood et al.

(10) Patent No.: US 10,202,341 B2
(45) Date of Patent: *Feb. 12, 2019

(54) COMPOSITIONS COMPRISING A REACTIVE MONOMER AND WITH A UREA OR URETHANE FUNCTIONAL GROUP

(71) Applicant: ISP Investments LLC, Wilmington, DE (US)

(72) Inventors: David K. Hood, Basking Ridge, NJ (US); Osama M. Musa, Bedminster, NJ (US)

(73) Assignee: ISP Investments LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/246,709

(22) Filed: Aug. 25, 2016

(65) Prior Publication Data

US 2017/0129856 A1    May 11, 2017

Related U.S. Application Data

(63) Continuation-in-part of application No. 13/521,456, filed as application No. PCT/US2011/020620 on Jan. 10, 2011, now abandoned.

(60) Provisional application No. 61/293,850, filed on Jan. 11, 2010.

(51) Int. Cl.
| | |
|---|---|
| *C07D 207/27* | (2006.01) |
| *G03G 9/087* | (2006.01) |
| *C09D 11/101* | (2014.01) |
| *C09D 11/106* | (2014.01) |
| *C09D 11/30* | (2014.01) |

(52) U.S. Cl.
CPC .......... *C07D 207/27* (2013.01); *C09D 11/101* (2013.01); *C09D 11/106* (2013.01); *C09D 11/30* (2013.01); *G03G 9/08708* (2013.01)

(58) Field of Classification Search
None
See application file for complete search history.

(56) References Cited

U.S. PATENT DOCUMENTS

| | | | |
|---|---|---|---|
| 2,882,262 A | | 4/1959 | Smith et al. |
| 3,417,054 A | | 12/1968 | Grosser et al. |
| 3,423,381 A | | 1/1969 | Grosser et al. |
| 3,783,151 A | | 1/1974 | Carlick et al. |
| 3,903,110 A | * | 9/1975 | Freyermuth ......... C07D 207/27 504/156 |
| 4,859,780 A | * | 8/1989 | Molock ..................... C08F 8/00 540/531 |
| 5,830,964 A | | 11/1998 | Liu et al. |
| 6,103,820 A | | 8/2000 | Blankenburg et al. |
| 6,458,888 B1 | | 10/2002 | Hood et al. |
| 6,605,359 B2 | | 8/2003 | Robinson et al. |
| 6,630,599 B1 | | 10/2003 | Singh et al. |
| 2002/0055585 A1 | | 5/2002 | Hood et al. |
| 2002/0058750 A1 | | 5/2002 | Hood et al. |
| 2010/0041846 A1 | | 2/2010 | Hood et al. |
| 2011/0293540 A1 | | 12/2011 | Hood et al. |
| 2012/0149861 A1 | | 6/2012 | Musa |
| 2013/0085230 A1 | | 4/2013 | Hood et al. |
| 2015/0337065 A1 | * | 11/2015 | Nam ..................... H01L 23/293 257/40 |

FOREIGN PATENT DOCUMENTS

WO    WO 2014/106972    * 10/2014

OTHER PUBLICATIONS

CAS Registry No. 1266326-05-9, Mar. 2011.*
Kadykov et al, Khimicheskaya Promysjenmost, vol. 4, pp. 209-210, 1982.
Original document, Kadykov et al, Khimicheskaya Promysjenmost, vol. 4, pp. 209-210, 1982.
International Search RePort of PCT Application No. PCT/US2011/020620 dated Mar. 17, 2011.

* cited by examiner

*Primary Examiner* — Erma C Cameron
(74) *Attorney, Agent, or Firm* — William J. Davis

(57) ABSTRACT

Disclosed herein are compositions comprising a reactive monomer, and, in particular, coating and/or reactive coating compositions. More particularly, compositions containing monomers comprising a lactam moiety, a urethane or urea functional group, and a polymerizable moiety are disclosed.

7 Claims, No Drawings

COMPOSITIONS COMPRISING A REACTIVE MONOMER AND WITH A UREA OR URETHANE FUNCTIONAL GROUP

This continuation-in-part patent application pursuant to 37 C.F.R § 1.53(b) claims the benefit of pending prior patent application Ser. No 13/521,456, filed Aug. 29, 2012.

FIELD OF THE INVENTION

The present application relates to compositions comprising a reactive monomer, and, in particular, to coating and/or reactive coating compositions. More particularly, the present application relates to compositions containing monomers comprising a lactam moiety, a urethane or urea functional group, and a polymerizable moiety and their use in coatings. Also disclosed are applications and compositions comprising coating solutions of a reactive monomer and the use of the compositions in printing processes and inks.

BACKGROUND OF THE INVENTION

Commercial printing processes are dominated by lithography, flexography, letterpress, screen printing and electrophotographic printing. Rapidly evolving technologies for sublimation/melt-type printing and ink-jet are becoming more commercially attractive processes. Increasing in influence of these printing technologies is curable ink systems.

A distinguishing feature of printing ink is its visual appearance. The color, transparency, intensity or density, and gloss often determine the suitability of the ink for a particular application. Another distinguishing feature of printing ink is its adhesion to surfaces, resistance to scratching and defacement, impact resistance, resistance to heat, resistance to solvents or other media, lightfastness, UV stability, and flexibility.

In many printing processes, once these challenges are met, the ink is then evaluated for suitability for color matching. Color matching often requires the use of one colored ink in concert with other different colored inks. In one example, International Commission on Illumination (CIE) color matching, provides for an increase in the color spectrum though a process of mixing primary colors (red, green, and blue) to produce secondary colors (cyan, magenta, and yellow) and myriads of possibilities between them. For such a system to function properly, the ink must be truly compatible, not only in physical/chemical properties, but in color properties too.

There are many raw materials employed in the manufacturing of ink products. The four basic components of a printing ink are pigments and dyes, resins, solvents, and additives. These components can be broken down into further details covering potential ingredients such as pigments and dyes, oils, resins, solvents, plasticizers, waxes, driers, chelating agents, anti-oxidants, surfactants, deodorants and fragrances, defoaming agents, adhesion promoters, photo-initiators, reactive diluents, oligomers, inhibitors, and laking agents. Not all of these ingredients will be used for all inks and some ingredients are capable of serving more than one purpose.

Viscosity is a key element to the physical properties and commercial performance capabilities of an ink system. As indicated in Kipphan's Handbook of Print Media: Technologies and Production Methods (Springer Verlag, New York, 2001) and Leach and Pierce's Printing Ink Manual (Kluwer, Boston, 1999), typical viscosity ranges for inks and coatings can vary depending on the particular printing process as provided below in Table 1.

TABLE 1

Typical Viscosity Ranges for Various Printing Processes

| Printing Process | Typical Viscosity Range (Pa * s) |
|---|---|
| Lithography | 2 to 30 |
| Offset | 40 to 100 |
| Letterpress | 50 to 150 |
| Sublimation and Melt-Type printing | solid at room temperature and melts at elevated temperature |
| Electrophotographic | ~0.1 to 10, for liquid toner Solid, for dry toner |
| Flexography | 0.05 to 0.5 |
| Gravure | 0.01 to 0.2 |
| Screen | 1.5 to 2.0 or higher |
| Ink-jet | ~0.001 to 0.1 |
| Intaglio | 9 to 25 |

Typical devices for measuring the viscosity of an ink system include capillary viscometers, falling sphere viscometers, flow cups (i.e., Zahn, Shell and Ford), rotational viscometers, cone and plate viscometers (i.e., Haake, TA Instruments), controlled stress rheometers, falling bar viscometers and the like.

As printing speeds become faster and materials more specialized, certain aspects of the printing process have evolved. For example, in some printing press applications, it is not uncommon to employ substrates that are pre-treated, by providing a primer coating to enable adhesion to the surface or surface treating with corona or flame, thereby enabling good ink performance on the substrate despite the added cost in materials and/or production time.

Printing technologies are applied to many different surfaces. For example, polyester film, polyolefin film (PE and PP), polycarbonate, polyimide film, metals (e.g., aluminum, steel, copper), glass, vinyl film, Tyvec® materials, canvas, polyvinylidene chloride films, paper, polyurethane, ceramics, wood and the like are examples of typically used substrates.

In curable ink systems, the polymerization process can be initiated by thermal effects or irradiation ($\alpha$, $\gamma\square$, and x-rays, UV, E-beam, and the like).

Among the properties that can be beneficially impacted by monomers are solution viscosity, cure speed, adhesion, impact resistance, toughness, coating hardness, surface tension, wetting, foaming, tensile strength, solvency, dispersive properties, flexibility, chemical resistance, abrasion resistance, and penetration.

SUMMARY OF THE INVENTION

The present application relates to compositions comprising a reactive monomer. More particularly, the present application relates to monomers comprising a lactam moiety, a urethane or urea functional group, and a polymerizable moiety. The disclosed compositions may be formulated as various products such as coatings, reactive coatings and inks.

In accordance with certain aspects, the composition may contain one or more reactive co-solvents or other monomers in addition to the reactive monomer.

A method of printing or coating a substrate using a composition containing the reactive monomer described herein is also provided.

DETAILED DESCRIPTION OF THE INVENTION

The singular forms "a," "an," and "the" include plural referents unless the context clearly dictates otherwise specified or clearly implied to the contrary by the context in which the reference is made. The terms "comprising" and "comprises of" include the more restrictive terms such as "consisting essentially of" and "consisting of."

The term "reactive monomer" throughout the specification and the claims is defined as a material comprised of a carbon-carbon double bond. When activated as described herein, the carbon-carbon double bond reacts with other carbon-carbon double bonds in the ink to form a polymeric material.

The term "curing" throughout the specification and the claims refers to the process of exposing a material to an appropriate energy source to polymerize the material, for example, converting a liquid to a solid. The resulting cured product is incapable of demonstrating a molecular weight as determined by gel permeation chromatography (GPC).

The term "lithography" throughout the specification and the claims refers to a printing process that employs a flat printing plate. The printable area is usually ink-receptive while the non-printable area repels ink.

The term "flexography" throughout the specification and the claims refers to a relief printing process. This process is rotary employing rubber or photopolymer plates and an ink system. Typically, printing is achieve via transfer of the ink from an anilox roller to a substrate.

The term "letterpress" throughout the specification and the claims refers to a relief printing process employing rubber or photopolymer plates and an ink system. Typically, printing is achieved via transfer of the ink from a roller and pressed into contact with the substrate.

The term "screen printing" throughout the specification and the claims refers to a stencil printing process. A rubber squeegee is employed to push ink through a stencil onto a substrate.

The term "ink-jet" throughout the specification and the claims refers to a computer controlled stream of ink droplets, ejected at high speed, onto a printing surface.

The term "electrophotographic" throughout the specification and the claims refers to a printing process whereby light is used to selectively discharge an electrostatic field, forming an electrostatically charged image. Toner of proper charge is then transferred to the substrate and fused to the surface by heat or other process.

Reactive monomers useful in accordance with the present application comprise a lactam moiety, a urethane or urea functional group, and a polymerizable moiety. These monomers may be represented by the structure:

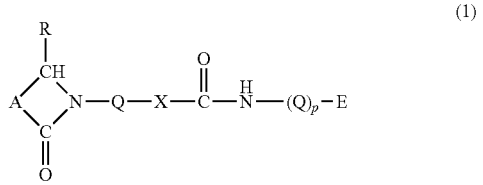

(1)

with the proviso that the reactive monomer is not a bis structure. "Bis" is a prefix meaning "twice" or "again" which is used in chemical nomenclature to indicate that a chemical group or radical appears twice in a molecule. "Bis" is sometimes used in chemical nomenclature instead of the prefix "di-".

Each of the follow generalized groups, A, E, p, Q, R, and —X—, in the above structure are described in more detail below.

The linker group —X— may be selected from —O— and

wherein R is defined below. As will be discussed in greater detail in the Synthesis section, the linker group represents the reactive union of parent reactants, e.g., an isocyanate-containing compound with a hydroxyalkyl lactam compound or an aminoalkyl lactam compound. With this definition of the linker group, the monomers described herein may be urethanes:

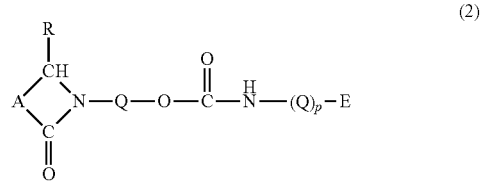

(2)

or ureas:

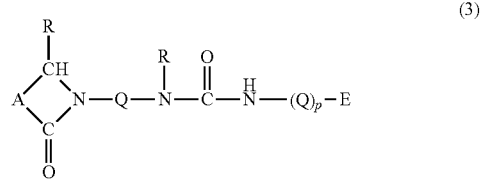

(3)

Group A represents an alkylene or alkenylene group comprising 2 to 50, more particularly 2 to 10, carbon atoms, wherein 2 to 4 carbon atoms reside in the lactam ring between the

group and the

group. In particular embodiments, -A- groups that may reside in the lactam ring between the

group and the

group include:

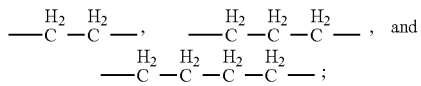

such that the formed lactam rings are pyrrolidone, piperidone, and caprolactam, respectively.

E represents a polymerizable moiety, examples of which include: alkylacrylamides, acrylates, allyl derivatives, benzoxanes, cinnamyls, epoxies, fumarates, maleates, maleimides, oxazolines, oxetanes, styrenes, vinyl acetates, vinyl acrylamides, vinyl amides, vinyl carbonates, vinyl ethers, vinyl imidazoles, vinyl lactams, vinyl pyridines, vinyl silanes, vinyl sulfones, and mixtures thereof.

Referring back to structure (1), the subscript p is selected from the group consisting of 0 and 1. When p equals 0, then a direct bond exists between the polymerizable moiety E and the urethane/urea nitrogen. Otherwise, when p equals unity then a spacer group Q exists between these two groups. Furthermore, when p equals unity it is noted that the two spacer groups Q in structures (1), (2), and (3) may be independently selected from each other.

Each of the spacer groups Q may be independently selected from functionalized and unfunctionalized alkylene, alkenylene, cycloalkylene and arylene groups, wherein any of the aforementioned groups may be with or without heteroatoms and linear or branched, typically containing from 1 to 20, more particularly 1 to 10 and in certain cases from 1 to 6 carbon atoms; and each R is independently selected from hydrogen, and functionalized and unfunctionalized alkyl, cycloalkyl, alkenyl, and aryl groups, wherein any of the aforementioned groups may be with or without heteroatoms and linear or branched, typically containing from 1 to 20, more particularly 1 to 10 and in certain cases from 1 to 6 carbon atoms.

In particular embodiments, A is selected from the group consisting of

meaning that the lactam ring is pyrrolidone and caprolactam, respectively. Thus, particular urethane structures (2) include:

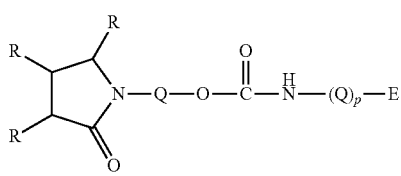

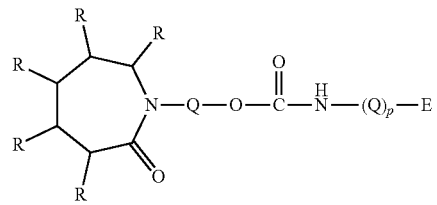

and particular urea structures (3) include:

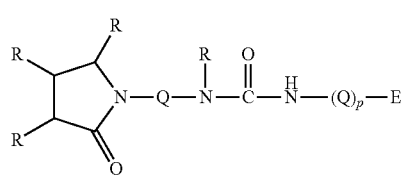

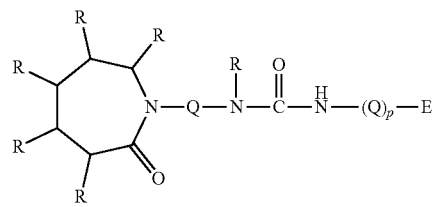

wherein the groups E, p, Q and R retain their earlier definitions.

By defining particular examples for the remaining groups, many compounds can be identified. Non-limiting examples of these molecules now will be given, with the understanding that one skilled in the art can identify additional A, E, p, Q, and R groups and thereby construct additional compounds suitable for use herein.

Given the many requirements and challenges for reactive materials in ink applications, there is a constant need for a new reactive monomers; certain aspects of the present application relate to energy curable, reactive monomers containing —C=C— functionalities.

In addition to the reactive monomers, the compositions disclosed herein may include reactive co-solvents. The reactive co-solvents may include (meth)acryl monomers or pre-polymers, a (meth)acryl ester of an epoxy type monomer or pre-polymer, and a urethane type monomers or pre-polymers. The reactive co-solvents typically include a carbon-carbon double bond capable of reacting with the polymerizable unit of the reactive monomers, which itself typically includes a carbon-carbon double. In one embodiment, a mixture of reactive co-solvents may be included in the formulation with the reactive monomer.

Examples of reactive co-solvents include but are not limited to 2-hydroxy methyl methacrylate (HEMA), 2-hydroxy ethyl acrylate (HEA), 2-phenoxy ethyl acrylate (PHEA), 2-ethylhexyl-diglycol acrylate, 2-(2-ethoxyethoxy) ethyl acrylate (EOEOEA), lauryl acrylate (LA), Stearyl acrylate (SA), isobornyl acrylate (IBOA), acrylic acid-2-ethylhexyl ester, isodecyl acrylate, acryloyl morpholine (ACMO), cyclic trimethylol-propane formal acrylate (CTFA), 3-(Methacryloyl amino)propyl]trimethylammonium chloride (MAPTAC), (3- Acrylamidopropyl)trimethylammonium chloride (APTAC), C8-C10 acrylate (ODA), isodecyl acrylate (ISODA), lauryl methacrylate (LM), stearyl methacrylate (SM), 2,2,2-Trifluoroethyl methacrylate, 2-Acrylamido-2-methyl-1-propanesulfonic acid, 2-Acrylamido-2-methyl-1-propanesulfonic acid sodium salt, [2-(Methacryloyloxy)ethyl]dimethyl-(3-sulfopropyl) ammonium hydroxide, [3-(Methacryloylamino)propyl]dimethyl(3-sulfopropyl)ammonium hydroxide inner salt, 1,6-hexanediol diacrylate (HDDA), dipropylene glycol diacrylate (DPGDA), tripropylene glycol diacrylate (TPGDA), 1,4-butanediol diacrylate (BDDA), Tripropylene glycol diacrylate (TPGDA), dipropyleneglycol diacrylate (DPGDA), Tripropylene glycol diacrylate (TRPGDA), 1,9-nonanediol diacrylate (NNDA), neopentyl glycol diacrylate (NPGDA), propoxylated neopentyl glycol diacrylate (NPG2PODA), polyethylene glycol (200) diacrylate (PEG (200)DA), polyethylene glycol (400) diacrylate (PEG(400) DA), polyethylene glycol (600) diacrylate (PEG(600)DA), ethoxylated bisphenol-A diacrylate (BPA2EODA), triethylene glycol diacrylate (TEGDA), triethylene glycol dimethacrylate (TEGDMA), glycerol propoxylated triacrylate (GPTA), diethylene glycol dimethacrylate (DEGDMA), ethoxylated bisphenol-A dimethacrylate (BPA10EODMA), trimethylolpropane triacrylate (TMPTA), pentaerythritol triacrylate (PET3A), ethoxylated tri-methylolpropane triacrylate (TMP3EOTA), propoxylated tri-methylolpropane triacrylate (TMP3POTA), propoxylated glyceryl triacrylate (GPTA), trimethylolpropane trimethylacrylate (TMPTMA), ethoxylated trimethylolpropane trimethacrylate (TMP3EOTMA), 2,2-dionol diacrylate, pentaerythritol tetraacrylate (PETA), neopentylglycol diacrylate hydroxypivalate, 2-acryloyloxyethylphthalic acid, 2-acryloyloxyethyl-2-hydroxyethylphthalic acid, dimethyloltricyclodecane diacrylate, 2-acryloyloxyethylsuccinic acid, nonylphenol ethylene oxide adduct acrylate, methoxy-polyethylene glycol acrylate, tetramethylolmethane triacrylate, dipentaerythritol hexaacrylate (DPHA), isocyanate-functional unsaturated acrylic ester resin, urethane diacrylates oligomers, urethane acrylates, modified urethane acrylates, polyester acrylates, modified bisphenol A diacrylate, phenoxy-polyethylene glycol acrylate, bisphenol A propylene oxide modified diacrylate, bisphenol A ethylene oxide adduct diacrylate, pentaerythritol triacrylate hexamethylenediisocyanate, urethane prepolymer, isoamyl acrylate, isomyristyl acrylate, isostearyl acrylate, carbitol acrylate, cyclohexyl acrylate, tetrahydrofurfuryl acrylate, 1,4-butane-diol-monoacrylate and/or diglycidyl ether of 1,4-butanediol, and the like. Mixtures of monomers may also be used.

Additional examples of reactive co-solvents include methyl vinylether, ethyl vinylether, propyl vinylether, n-butyl vinylether, t-butyl vinylether, 2-ethylhexyl vinylether, n-nonyl vinylether, lauryl vinylether, cyclohexyl vinylether, cyclohexylmethyl vinylether, 4-methylcyclohexylmethyl vinylether, benzyl vinylether, dicyclopentenyl vinylether, 2-dicyclopentenoxyethyl vinyl ether, methoxyethyl vinylether, ethoxyethyl vinylether, butoxyethyl vinyl ether, methoxyethoxy vinylether, ethoxyethoxyethyl vinylether, methoxypolyethylene glycol vinylether, tetrahydrofurfuryl vinylether, dodecyl vinylether, diethylene glycol monovinylether, 2-hydroxyethyl vinylether, 2-hydroxypropyl vinylether, 4-hydroxybutyl vinylether, 4-hydroxymethylcyclohexylmethyl vinylether, polyethylene glycol vinylether, chloroethyl vinylether, chlorobutyl vinylether, phenylethyl vinylether, phenoxypolyethylene glycol vinylether, ethylene glycol divinylether, butylenes glycol divinylether, hexandiol divinylether, bisphenol A alkyleneoxide divinylethers, bisphenol F alkyleneoxide divinylethers, propyleneoxide adducts of trimethylolpropane trivinylether, triethylene glycol divinylether, cyclohexane dimethanol divinylether, N-vinyl-2-pyrrolidone (VP), N-vinyl caprolactam (VCap), N-vinyl imidazole (VI), n-vinyl amides, 4-vinyl pyridine, 2-vinyl pyridine, styrene, 5-vinyl-2-norbornene and the like.

Non-limiting examples of monofunctional epoxy compounds include phenyl glycidylether, p-tert-butylphenyl glycidylether, butyl glycidylether, 2-ethylhexyl glycidylether, allyl glycidylether, 1,2-butyleneoxide, 1,3-butadienemonooxide, 1,2-epoxydodecane, epichlorohydrin, 1,2-epoxydecane, styreneoxide, cyclohexeneoxide, 3-methacryloyloxymethylcylcohexeneoxide, 3-acryloyloxymethylcylcohexeneoxide, 3-vinylcylcohexeneoxide, and the like.

Non-limiting examples of multifunctional epoxy compounds include 3,4-epoxycyclohexylmethyl-3,4-epoxycyclohexane carboxylate, 3-ethyl-3-((ethyloxetane-3-yl) methoxy) methyl)oxetane, bisphenol A diglycidylether, bisphenol F diglycidylether, bisphenol S diglycidylether, brominated bisphenol A diglycidylether, brominated bisphenol F diglycidylethers, brominated bisphenol S diglycidylether, epoxy novolak resins, hydrogenated bisphenol A diglycidylethers, hydrogenated bisphenol F diglycidylethers, hydrogenated bisphenol S diglycidylethers, 3,4-epoxycyclohexylmethyl-3',4'-epoxycyclohexanecarboxylate, 2-(3,4-epoxycyclohexyl-5,5-spiro-3,4-epoxy) cyclohexane-meta-dioxane, bis(3,4-epoxycyclohexylmethyl) adipate, vinylcylcohexeneoxide, 4-vinylepoxycyclohexane, bis(3,4-epoxy-6-methylcyclohexylmethyl) adipate, 3,4-epoxy-6-methylcyclohexyl-3',4'-epoxy-6'-methylcyclohexane carboxylate, methylene-bis(3,4-epoxycyclohexane), dicyclopentadiene diepoxide, ethylene glycol di(3,4-epoxycyclohexylmethyl)ether, ethylene bis(3,4-epoxycyclohexanecarboxylate), epoxyhexahydrodioctyl phthalate, epoxyhexahydrodi-2-ethylhexyl phthalate, 1,4-butanediol diglycidylether, 1,6-hexanediol diglycidylether, glycerol triglycidylether, trimethylolpropane triglycidylether, polyethylene glycol diglycidylether, polypropylene glycol diglycidylether, 1,1,3-tetradecadienedioxide, limonenedioxide, 1,2,7,8-diepoxyoctane, 1,2,5,6-diepoxycyclooctane, and the like.

Compositions disclosed herein may be cured, cross-linked or polymerized by any appropriate method. For example, polymerization of a reactive solution comprising a polymerizable polymer or monomers may be carried out by employing any of the methods disclosed in "Principles of Polymerization" 4th edition, 2004, Wiley by George Odian, the contents of which are hereby incorporated by reference. Various techniques or methods may be employed including, but not limited to, exposure to UV-radiation, UV-LED, laser beam, electron beam, and/or gamma irradiation, or other high-energy source, and free-radical, cationic, anionic, or thermal polymerization, which may occur in the presence of suitable initiator(s) such as photoinitiators, free-radical initiators, anionic or cationic initiators, and thermal initiators. Suitable sources of radiation include, but are not limited to, mercury, xenon, halogen, and carbon arc lamps, sunlight, and radioactive sources.

A photoinitiator may be added to the compositions herein to initiate polymerization upon exposure of the composition to radiation. Suitable photoinitiators include those selected from the following non-limiting group of compounds: 2-hydroxy-2-methyl-1-phenylpropane-1-one, 1-hydroxycyclohexyl phenyl ketone, and 2-methyl-1-1-[4-(methylthio)phenyl]-2-morphorinopropane-1-on; benzoins e.g., benzyl dimethyl ketal; benzophenones such as benzophenone, 4-phenylbenzophenone, and hydroxybenzophenone; thioxanthones such as isopropylthioxanthone and 2,4-diethylthioxanthone; acylphosphine oxides; and other special initiators such as methyl phenyl glyoxylate; bis[4-(di(4-(2-hydroxyethyl)phenyl)sulfoniolphenyl sulfide], a mixture of bis[4-diphenylsulfonio]phenyl)sulfide bis(hexafluoroantimonate and diphenyl-4-thiophenoxyphenylsulfonium hexafluoroantimonate, bis[4-(di(4-(2-hydroxyethyl)phenyl) sulfoniolphenyl sulfide], 5-2,4-cyclopentadiene-1-yl-[(1,2,3,4,5,6-.eta.)-(1-methylethyl-)benzene]-iron (1+)-hexafluorophosphate(1-)), 4-(2-hydroxytetradecanyloxy) diphenyliodonium hexafluoroantimonate, (4-hydroxynaphtyl) dimethylsulfonium hexafluoroantimonate), triphenylsulfonium hexafluorophosphate, triphenylsulfonium hexafluoroantimonate, 4-methoxyphenyldiphenylsulfonium hexafluoroantimonate, 4-methoxyphenyliodonium hexafluoroantimonate, bis (4-tert-butylphenyl)iodonium tetrafluoroborate, (bis(4-tert-butylphenyl)iodonium hexafluorophosphate), (bis(4-tert-phenyl)iodonium hexafluoroantimonate), (bis [4-(diphenylsulfonio)phenyl]sulfide bis (hexafluorophosphate)), aryldiazonium salts, diaryliodonium salts, triaylsulfonium salts, tri aryl selenonium salts, dialkylphenacylsulfonium salts, triarylsulfoxonium salts, aryloxydiarylsulfonium salts, and the like, for example, triphenylsulfonium hexafluorophosphate, methyidiphenylsulfonium hexafluorophosphate, dimethylphenylsulfonium hexafluorophosphate, diphenyinapththylsulfonium hexafluorophosphate, di(methoxynapththyl) methylsulfonium hexafluorophosphate, (4-octyloxyphenyl) phenyl iodonium hexafluoro antimonate, (4-octyloxyphenyl) diphenyl sulfonium hexafluoro antimonate, (4-decyloxyphenyl) phenyl iodonium hexafluoro antimonite, (4-dodecyloxyphenyl)diphenyl sulfonium hexafluoroantimonate. Particularly employed photoinitaitors include 10-biphenyl-4-yl-2-isopropyl-9H-thixanthen-10-ium hexafluorophosphate, 4,4'-dimethyl iodonium hexafluorophosphate, mixed triarylsulfonium hexafluorophosphate salts and reaction products of a polyol and 10-(2-carboxymethoxy)-biphenyl-4yl-2-isopropyl-9-oxo-9H-thioxanthen-10-ium hexafluorophosphate. Further, these photoinitiators may be used alone or in combination thereof. Alternatively, the photoinitiator may be used by mixing it with one or more photopolymerization accelerators, such as a benzoic acid (e.g., 4-dimethylaminobenzoic acid) or a tertiary amine, in any appropriate ratio. The photoinitiator may be added to the photopolymerizable composition in the range of about 0.1% to about 20% by weight.

In accordance with certain embodiments, the polymerizable material may be reacted through free-radical polymerization in the presence of a free-radical initiator. Suitable free radical initiators for polymerization include, but are not limited to, various derivatives of peroxides, peresters and/or azo compounds. More particularly, the free-radical initiator may be selected from dicumyl peroxide, dibenzoyl peroxide, 2-butanone peroxide, tert-butyl perbenzoate, di-tert-butyl peroxide, 2,5-bis(tert-butylperoxy)-2,5-dimethylhexane, bis (tert-butyl peroxyisopropyl)benzene, and tert-butyl hydroperoxide), diacyl peroxides, cumene hydroperoxide, dialkyl peroxides, hydroperoxides, ketone peroxides, monoperoxycarbonates, peroxydicarbonates, peroxyesters, and peroxyketals, including tertiary butyl perbenzoate, tertiary butyl peroctoate in diallyl phthalate, diacetyl peroxide in dimethyl phthalate, dibenzoyl peroxide, 1-hydroxy cyclohexyl-1-phenyl ketone, his (2,4,6-trimethyl benzoyl)phenyl phosphine, benzoin ethyl ether, 2,2-dimethoxy-2-phenyl acetophenone, di(p-chlorobenzoyl) peroxide in dibutyl phthalate, di(2,4-dichlorobenzoyl) peroxide with dibutyl phthalate, dilauroyl peroxide, methyl ethyl ketone peroxide, cyclohexanone peroxide in dibutyl phthalate, 3,5-dihydroxy-3,4-dimethyl-1,2-dioxacyc lopentane, t-butylperoxy (2-ethyl hexanoate), caprylyl peroxide, 2,5-dimethyl-2,5-di (benzoyl peroxy) hexane, 1-hydroxy cyclohexyl hydroperoxide-1, t-butyl peroxy (2-ethyl butyrate), 2,5-dimethyl-2,5-bis(t-butyl peroxy) hexane, cumyl hydroperoxide, diacetyl peroxide, t-butyl hydroperoxide, ditertiary butyl peroxide, 3,5-dihydroxy-3,5-dimethyl-1,2-oxacyclopentane, and 1,1-bis(t-butyl peroxy)-3,3,5-trimethyl cyclohexane and di-(4-t-butyl cyclohexyl) peroxydicarbonate, azo compounds such as azobisisobutyronitrile and azobiscyclohexanenitrile (e.g., 2,2'-azobis(2-methyl-propanenitrile), 2,2'-azobis(2-methylbutanenitrile), and 1,1'-azobis (cyclohexanecarbonitrile)) and the like including mixtures and combinations thereof.

Alternatively, the free-radical initiators disclosed above may be used for thermal based polymerization alone or as mixtures thereof. Other suitable thermal initiators include 2,2'-azobis (2,4-dimethylpentanenitrile), 2,2'-azobis (2-methylpropanenitrile), 2,2'-azobis (2-methylbutanenitrile), peroxides such as benzoyl peroxide, and the like. In one embodiment, the thermal initiator is 2,2'-azobis(isobutyronitrile).

Polymers produced as a result of polymerization, curing or crosslinking of the compositioins disclosed herein can be analyzed by any suitable techniques to characterize the product. Especially useful techniques include nuclear magnetic resonance (NMR) (1H-NMR, 13C-NMR) spectroscopy, FT-IR spectroscopy, gas chromatography (GC), and gel permeation chromatography (GPC) in order to decipher polymer identity, residual monomer concentrations, polymer molecular weight, and polymer molecular weight distribution.

The compositions disclosed herein may also include various optional additives.

According to certain embodiments, a colorant may be included in the compositions. The colorant may be in the form of a pigment or dye. Combinations of pigments and dyes are also envisioned. Examples of suitable pigments are described in Hunger's "Industrial Organic Pigments," Itoh's "Dictionary of Pigments," and Leach and Pierce's "Printing Ink Manual."

Examples of yellow colored, organic and inorganic, pigments include C.I. Pigment Yellow 1, C.I. Pigment Yellow 74, azo pigments such as C.I. Pigment 12 and C.I. Pigment Yellow 17 and the like.

Examples of black colored pigments include carbon black, titanium black, aniline black, and the like.

Examples of white colored pigments include basic lead carbonate, zinc oxide, barium sulfate, titanium oxide, silver white, strontium titanate, and the like.

Examples of red colored pigments include naphthol red (C.I. Pigment Red 2), C.I. Pigment Red 3, C.I. Pigment Red 176 and C.I. Pigment Red 23 and the like.

Examples of green colored pigments include phthalocyanine green (C.I. Pigment Green 7), C.I. Pigment Green 36, and C.I. Pigment Green 1 and the like.

Examples of blue colored pigments include phthalocyanine blue (C.I. Pigment Blue 15:3), C.I. Pigment Blue 15:6, and C.I. Pigment Blue 16 and the like.

In dispersing the pigment, dispersing machines and dispersants may be employed. Typical dispersing machines include agitators, ball mills, bead mills, colloid mills, Cowles mixers, Henschel mixers, homogenizers, jet mills, John mills, kneaders, pearl mills, roll mills, sand mills, STS mills, Tex mills, ultrasonic wave homogenizers, wet jet mills and the like. Typical dispersants include carboxylic acids comprised of hydroxyl groups, long chain polyaminoamide salts with high molecular weight acid esters, high molecular weight polycarboxylic acid salts (Na and NH4), alkyl pyrrolidones, a reactive monomer, high molecular weight copolymers, styrene acrylates, modified polyacrylates, polyvalent aliphatic carboxylic acids, naphthalenesulfonic acid/formalin condensates, polyoxyethylene alkylphosphoric esters, polyvinyl pyrrolidones, copolymers of vinyl pyrrolidone/vinyl acetates, alkylated polyvinyl pyrrolidones (alkylated with C4, C12, C20, C30, and the like), poly(maleic anhydride-co-methyl vinylether), poly(maleic anhydride-co-acrylic acid), copolymers of maleic anhydride, poly(tetrahydrofuran), Solsperse® dispersants (Zeneca), Zetasperse® Z-2100 and Z-2300 additives (Air Products), Surfynol® surfactants (104, 111, 121, 131, 136, 171, and 231(Air Products)), Tamol™ dispersant (731 and 1124 (Rohm and Haas)), Troysperse® 90W dispersant (Troy), AMP-95™ 2-amino-2-methyl-1-propanol solution (ANGUS Chemie GmbH), BYK®-346 additive (BYK), and the like.

Examples of blue colored dyes include Acid Blue 1, Basic Blue 1 and C.I. Solvent Blue 7 and the like.

Examples of red colored dyes include Acid Red 18, Basic Red 1 and C.I. Solvent Red 8 and the like.

Examples of green colored dyes include Acid Green 1 and Basic Green 1 and the like.

Examples of black colored dyes include C.I. Solvent Black 5 and the like.

According to certain embodiments, the composition may also contain an oil. Oils are typically classified as drying oils or non-drying oils. Drying oils are characterized by the presence of unsaturated —CH=CH— groups. Examples of drying oils include glycerides or triglycerides of fatty acids. Specific examples include oils of linseed, tung, oiticica, dehydrated castor, fish, and soya bean. Examples of non-drying oils include mineral, castor, and petroleum distillates.

In accordance with some embodiments, the composition may include a resin, or high molecular weight polymer. Examples of useful resins include acrylic polymers, polyvinylbutyral, polyurethanes, polyisocyanates, polyamides, polyesters, epoxies and polyepoxides, polyphenols, polycarbonates, polyvinylformal, shellac, vinylic, rubber based, waxes rosin, maleic resin and esters, manila copal, asphalts, starch and dextrin, gum Arabic, rosin modified phenolics, alkyds, terpenes, polystyrene, styrenic copolymers, styrene acrylates, silicone resins, alkylated urea formaldehyde resins, alkylated melamine formaldehyde resins, polyimides, poly(amide-imide) resins, chlorinated rubber, cyclized rubber, polyvinyl acetates, polyvinyl alcohols, alkylated polyvinyl alcohols, ketones resins, nitrocelluloses, ethyl cellulose, ethyl hydroxyethyl cellulose, cellulose acetate propionate, cellulose acetate butyrate, sodium carboxymethyl cellulose, polyethylene glycols and the like.

One or more solvents may also be included in the composition. Suitable solvents include those disclosed in the Industrial Solvents Handbook, 4ed. edited by E. W. Flick (Noyes Daya Corp, Park Ridge, N.J., 1991). Additional insight to solvent selection is also available in the Polymer Handbook, 4ed. edited by J. Brandrup, E. H. Immergut, and E. A. Grulke (John Wiley, New York, 1999), and in particular, the section entitled Solubility Parameters Values by E. A. Grulke. These references are hereby incorporated by reference.

Examples of useful solvents include hydrocarbon solvents (e.g., white spirit and paraffin oils, low and high boiling), aromatic hydrocarbons (e.g., toluene, xylene, paraffins, and naphthenes), alcohols (e.g., ethanol, n-propyl, isopropyl, n-butyl), alicyclic alcohols (e.g., cyclohexanol), glycols (e.g., monoethylene, monopropylene, hexylene, diethylene, dipropylene, triethylene), glycerin, ketones (e.g., acetone, butan-2-one, hexone, sexton, isophorone, diacetone alcohol), esters (ethyl acetate, isopropyl acetate, n-butyl acetate), n-methyl-2-pyrrolidone, γ-butyrolactone and the like.

The compositions may also include a plasticizer. Examples of useful plasticizers include abietates, adipates, alkyl pyrrolidones, alkylated caprolactams, benzoates, butyrates, citrates, epoxidized compounds, phthalates, polyester, polyol esters, ricinoleates, sebacates, stearates, and sulphonamides. Additional information relating to plasticizers can be found in the National Printing Ink Research Institute (NPIRI) "Raw Materials Data Handbook" (Volume 2). Specific examples of suitable plasticizers include triethyl citrate, epoxidized soya bean oils, dimethyl phthalate, glyceryl triacetate, butyl ricinoleate, butyl stearate, n-octyl-2-pyrrolidone, n-dodecyl-2-pyrrolidone, n-cocoyl-2-pyrrolidone, n-hydrogenated tallowyl-2-pyrrolidone and the like.

According to certain embodiments, the composition may include a wax. Examples of useful waxes include polyethylene, polytetrafluoroethylene, fatty acid amides (i.e., stearamide), petroleum (e.g., paraffins, slack, scale, jelly, microcrystalline, ceresin, montan, montan esters), beeswax, carnauba, shellac, Japan, candelilla, lanolin, alkylated polyvinyl pyrrolidones (alkylated with C4, C12, C20, C30, and the like), and the like.

The composition may also include a drier. Examples of useful driers include oil soluble soaps (formed from octoates, resonates, naphthenates, tallates, linoleates), cobalt, cobalt acetate, manganese, cerium, zirconium, lithium, calcium, zinc, lead acetate, manganese borate and the like.

A chelating agent may be also be included in the composition. Examples of useful chelating agents include ethylenediaminetetra-acetic acid and sodium salts, nitrilotriacetic acid salts, sodium salts of diethylenetriamine-acetic acid, heptonates, alkanolamines, dimethyl glyoxime and the like.

According to particular embodiments, the composition may include an anti-oxidant. Examples of useful anti-oxidants include eugenol, hydroquinone, pyrocatechol, guaiacol, butylated hydroxytoluene, butylated hydroxyanisole, methyl ethyl ketoxime, butylaldoxime, cyclohexanone oxime and the like.

According to some embodiments, the composition may include a surfactant. Surfactants can also be employed in the presence of defoaming agents such as polydimethyl siloxanes and derivatives thereof. Examples of useful surfactants include anionic (e.g., alkali metal soaps, ammonium and ammonium salts of long chain fatty acids), cationic (e.g., quaternary fatty ammonium halides, acetates, or sulphates), non-ionic (e.g., polyethylene oxide chains attached to hydrocarbons), amphoteric and the like.

Deodorants and/or fragrances may be included in the composition. Examples of useful deodorants and fragrances include amyl and methyl salicylate, vanillin, citron, cedarwood, peppermint, lavender, carnation and the like.

The composition may also include an adhesion promoter. Examples of useful adhesion promoters include titanium acetyl-acetonate, polyfunctional aziridines, polyethylene imines, chlorinated polyolefins, pentahydroxy(tetradecanoato) di-chromium, octadecanoato chromic chloride hydroxide, glycidoxy (epoxy) functional methoxy silane,☐ β-(3,4-epoxycyclohexyl) ethyltriethoxysilane and the like.

The composition may also include an inhibitor. Examples of useful inhibitors include hydroquinone, hydroquinone monomethyl ether, hydroquinone monopropyl ether, hydroquinone monobenzyl ether, amyl quinine, amyloxyhydroquinone, n-butylphenol, phenol, 4-methoxyphenol (MEHQ), phenothiazine, nitrobenzene and phenolic-thio compounds, alone or in combination thereof.

Laking agents may be included in the composition. Examples of useful laking agents include tannic acid and derivatives, shellac, maleic acids and the like.

According to certain embodiments, silica may be included in the composition. Examples of useful silicas include fumed, precipitated, gel, colloidal and the like.

In a particular embodiment of the invention, the composition may include a stabilizer to inhibit premature cross-linking. Examples of suitable stabilizers include, but are not limited to, hydroquinone, hydroquinone monomethyl ether, hydroquinone monopropyl ether, hydroquinone monobenzyl ether, amyl quinine, amyloxyhydroquinone, n-butylphenol, phenol, 4-methoxyphenol (MEHQ), phenothiazine, nitrobenzene and phenolic-thio compounds, alone or in combination thereof.

According to certain aspects, the composition may also include one or more additives in conventional quantities which may impart enhancement in the desired composition. Potential additives include, but are not limited to, slip modifiers, thixotropic agents, laponites, flow or rheology control agents, UV-light absorbers, fungicides, bactericides, organic/inorganic filler particles (e.g., clays, kaolins), leveling agents, antistatic agents, viscosity modifiers, therapeutic and/or preventive medicaments, and other ingredients apparent to those skilled in the art.

The compositions disclosed herein may include the reactive monomer as about 1 to about 50% by weight of the composition and the co-solvent, when present, as about 4 to about 80% by weight of the composition. Additionally, the compositions may include an initiator such as a photoinitiator or a polymerization initiator such as a free-radical initiator, a cationic initiator, an anionic initiator, or a thermal initiator as about 1 to about 10% by weight of the composition. If a colorant is included in the composition it may be present as about 1 to about 50% by weight of the composition. Other additives or components may be present in the composition as about 0.05 to about 60% by weight of the composition.

In one embodiment, the compositions disclosed herein include a resulting polymer produced by curing, cross-linking, or polymerizing a composition containing a reactive monomer. The compositions may be formulated for various applications such as industrial, personal care, household and pharmaceutical applications. Exemplary and non-limiting applications of the proposed compositions are in the field of coating-UV curable inks, newspaper inks, packaging inks, lithographic inks, offset inks, gravure inks and plates, flexographic inks and plates, screen inks, ink-jet inks, RFID devices, adhesive inter-layers, adhesion promoters, substrate penetrants, varnishes, labels, food wrappers, labels and colors for toys, labels and colors for pencils, labels and colors for comics, inks for postal application, inks for monetary application, inks for official government documents, over print varnish, visual identification, security inks, packaging, shrink wraps, container sleeves, metal inks and coatings, and anti-fog surfaces. The compositions may be produced as solid, liquid or powder or as a solution. These formulations may be applied to various surfaces as applicable to their intended use, for example, to paper, to metal such as steel, iron, copper, brass, gold, silver, and aluminum; to plastic such as vinyl, polyolefins such as polyethylene and polypropylene, Tyvec® materials, polyester, PVDC, and nylon; to glass; and to textiles.

In another embodiment, the compositions may be adhesive compositions that include the reactive monomer and reactive co-solvents as described above.

The compositions disclosed herein may be characterized as being conductive, metallic, pearlescent, fluorescent, and/or as exhibiting or having a thermal transition or phase change.

In one embodiment, the compositions may optionally include carbon nanostructures such nano-onions, horns, tubes, rods, wires, cones, dots, whiskers, filaments, nano-diamond, and graphene sheets. In another embodiment, the compositions disclosed herein may optionally include quantum dots.

Particular aspects of the present invention are illustrated in detail by way of the following examples. The examples are for illustration and are not intended to be limiting.

EXAMPLE 1

UV Curing Ink Base

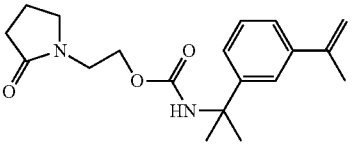 [SMILES: C=C(C)c1cccc(C(C)(C)NC(=O)OCCN2CCCC2=O)c1]

| Material | Supplier | Mass (g) |
|---|---|---|
| N-Vinyl Pyrrolidone | ISP | 9.875 |
| Reactive monomer | | 9.875 |
| Irgacure 184 | Ciba | 3.0 |
| PETA-4 (SR 295) | Sartomer | 76.75 |
| Surfactant DC-193 | Dow Corning | 0.5 |
| Total | | 100 |

EXAMPLE 2

Offset Lithographic Ink

Employing the teachings of Leach and Pierce's Printing Ink Manual (Kluwer, Boston, 1999) (the contents of which are hereby incorporated by reference) as a guide for the production of a standard dry offset lithographic ink, a modified formulation employing a reactive monomer was designed and is presented below:

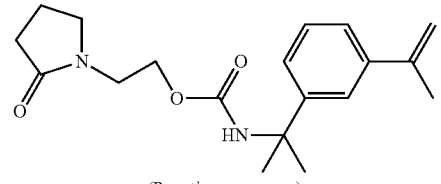

| Raw Material | w/w % |
|---|---|
| Pigment | 18.0 |
| Acrylate prepolymer | 30.0 |
| Modifying hard resin | 25.0 |
| (Reactive monomer) | 16.0 |
| Photo-initiator and amine synergist | 9.0 |
| Polyethylene wax | 1.0 |
| Silicone fluid | 1.0 |

U.S. Pat. No 7,232,851 and WO 2003/014239 (the contents of which are hereby incorporated by reference) disclose information relating to lithographic inks that can be utilized as guides for the production of a lithographic inks.

EXAMPLE 3

Flexographic Ink

Employing the teachings of U.S. Pat. No 7,291,658 B2 (the contents of which are hereby incorporated by reference) as a guide for the production of a standard white radiation-curable flexographic ink, a modified formulation employing a reactive monomer was designed and is presented below:

| Raw Material | Description | Parts (w/w) |
| --- | --- | --- |
| Pigment | R-706 | 40.0 |
| Ashland D-30R | Ashland resin for grinding pigments | 17.5 |
| Ashland F-126R | Ashland resin | 28.0 |
|  | Reactive Monomer | 10.0 |
| LG-37 | Reactive defoaming agent | 1.0 |
| BYK 019 | Silicone defoamer | 0.5 |
| ViaCure LX | UCB photoinitiator vehicle for light ink applications | 3 |

EXAMPLE 4

Letterpress Ink

Employing the teachings of U.S. Pat. No 6,620,227 (B1) (the contents of which are hereby incorporated by reference) as a guide for the production of a UV curable CF (coated front) ink, a modified formulation employing a reactive monomer was designed and is presented below:

| Raw Material | Description | Parts (w/w) |
| --- | --- | --- |
| KC 98-1410 UV from Kohl & Madden Ink | UV curable ink base | 25.17 |
| Bis-(3-allyl-4-hydroxy phenyl) sulfone | Acidic color developer | 50.34 |
| 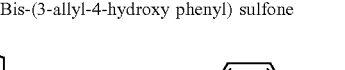 | Reactive monomer and reactive solvent | 23.49 |
| Darocure 4265 from Ciba | Photo-initiator | 1.00 |

EXAMPLE 5

Screen Printing Ink

Employing the teachings of U.S. Pat. No 7,291,658 B2 (the contents of which are hereby incorporated by reference) as a guide for the production of a standard white screen-ink, a modified formulation employing the reactive monomer was designed and is presented below:

| Raw Material | Description | Parts (w/w) |
|---|---|---|
| Pigment | R-706 | 41.2 |
| ViaScreen 515 | UCB Vehicle for screen printing applications | 30.1 |
| Ebecryl 110 | 2-Phenoxyethyl acrylate | 18.8 |
| (reactive monomer structure) | Reactive Monomer | 7.21 |
| LG-37 | Reactive defoaming agent | 1.0 |
| BYK 019 | Silicone defoamer | 0.5 |
| ViaCure LX | UCB photoinitiator vehicle for ink applications | 6 |

Additional teachings can be found in U.S. Pat. No 5,395,863 (the contents of which are hereby incorporated by reference).

EXAMPLE 6

Screen Printing Ink

Employing the teachings of U.S. Pat. No 4,418,138 A (the contents of which are hereby incorporated by reference) as a guide for the production of a standard black screen-ink, a modified formulation employing the reactive monomer was designed and is presented below:

| Raw Material | Parts (w/w) |
|---|---|
| Catofor 06 | 1.0 |
| 2-(carboxymethoxy)thioxanthone | 0.5 |
| Ethanol | 5.0 |
| Polyethylene glycol 200 diacrylate | 10.5 |

| Raw Material | Parts (w/w) |
|---|---|
| (reactive monomer structure) | 4.5 |
| Uvecryl P101 | 2.0 |
| 20% Gohsenol KP08 solution | 50.0 |
| Anthrasol Blu-Black 1RD | 0.5 |
| Polyethylene glycol 200 | 1.0 |

EXAMPLE 7

Ink-Jet Printing Ink

Employing the teachings of WO 2007/036692 (A1) (the contents of which are hereby incorporated by reference) as a guide for the production of a standard UV inkjet ink, a modified formulation employing a reactive monomer was designed and is presented below:

| Raw Material | Description | Parts (w/w) |
|---|---|---|
| Polyethylene glycol 200 diacrylate | oligomer | 9 |
| Ethoxylated (20) trimethylolpropane triacrylate | monomer | 4.5 |
| (reactive monomer structure) | Reactive monomer | 24.8 |
| Water | | 44.9 |
| Cab-O-Jet 300 | Carbon black pigment with carboxylate surface treatment for water application | 12.5 |
| Irgacure 2959 | Photo-initiator | 4 |
| FC4430 | fluorosurfactant | 0.2 |

EXAMPLE 8

Electrophotographic Printing Ink

Employing the teachings of U.S. Pat. No 5,332,644 A (the contents of which are hereby incorporated by reference) as a guide for the production of a standard electrophotographic coating, a modified formulation employing a reactive monomer was designed and is presented below.

| Raw Material | Parts (w/w) |
|---|---|
| Benzimidazole perylene (BZP) | 9.25 |
| (reactive monomer) | 36.3 |
| Styrene | 54.45 |

EXAMPLE 9

Intaglio Printing Ink

Employing the teachings of U.S. Pat. No 6,787,583 (B2) (the contents of which are hereby incorporated by reference) as a guide for the production of a intaglio UV ink, a modified formulation employing a reactive monomer was designed and is presented below:

| Raw Material | Parts (w/w) |
|---|---|
| Ebecryl 2002 | 46.6 |
| Montan Wax | 4.0 |
| (Reactive Monomer) | 1.5 |
| Emulsifier | 1.5 |
| UV Stabilizer | 2.0 |
| Irgalite Red 8B | 8.0 |
| CaCO$_3$ | 30.0 |
| Esacure ITX | 2.6 |
| Irgacure 369 | 3.8 |

EXAMPLE 10

Printing Plate

Employing the teachings of U.S. Pat. No 4,011,084 (A) (the contents of which are hereby incorporated by reference) as a guide for the production of a UV curable printing plate, a modified formulation employing a reactive monomer was designed and is presented below:

| Raw Material | Parts (w/w) |
|---|---|
| Polyurethane/ester diacrylate | 75 |
| (Reactive monomer) | 25 |
| Benzoin methyl ether | 1 |
| Potassium salt of N-nitrosocyclohexylhydroxylamine | 0.05 |

The invention has been described in detail with reference to particular embodiments thereof, but it will be understood that variations and modifications can be effected within the spirit and scope of the invention.

What is claimed is:

1. A composition comprising a reactive monomer having the structure

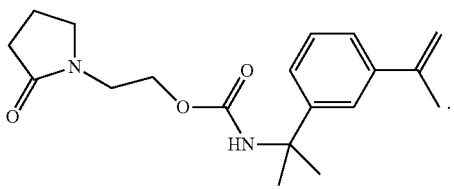 [SMILES: C=C(C)c1cccc(C(C)(C)NC(=O)OCCN2CCCC2=O)c1]

.

2. The composition of claim 1, further comprising a component selected from the group consisting of photoinitiators, free-radical initiators, cationic initiators, anionic initiators, and thermal initiators.

3. The composition of claim 1, further comprising a component selected from the group consisting of colorants, dispersants, oil, resins, solvents, plasticizers, waxes, driers, chelating agents, anti-oxidants, surfactants, deodorants, fragrances, adhesion promoters, inhibitors, laking agents, silica, stabilizers, and defoaming agents.

4. The composition of claim 3, comprising a colorant that includes a carbon pigment.

5. The composition of claim 1 , wherein the composition is a lithographic ink, a flexographic ink, a gravure ink, a letterpress ink, a screening printing ink, ink-jet printing ink, an electrophotographic ink, an intaglio printing ink, or a collotype printing ink.

6. The composition of claim 1, wherein the composition is a curable composition.

7. The composition of claim 6, wherein the composition is a curable ink or coating composition.

* * * * *